US005269293A

United States Patent [19]

Löser et al.

[11] Patent Number: 5,269,293

[45] Date of Patent: Dec. 14, 1993

[54] COOLING DEVICE FOR COOLING BREATHING GAS IN A RESPIRATORY PROTECTION DEVICE

[75] Inventors: Ralf E. Löser, Kreuzkamp; Christoph Maurer, Bad Schwartau, both of Fed. Rep. of Germany

[73] Assignee: Dragerwerk Aktiengesellschaft, Lübeck, Fed. Rep. of Germany

[21] Appl. No.: 757,626

[22] Filed: Sep. 11, 1991

[30] Foreign Application Priority Data

Sep. 13, 1990 [DE] Fed. Rep. of Germany ....... 4029084

[51] Int. Cl.[5] ...................... A61M 16/00; A62B 7/00; F24F 5/00

[52] U.S. Cl. .......................... 128/204.15; 128/204.18; 128/205.22

[58] Field of Search ...................... 128/204.15, 204.16, 128/205.27, 205.28, 205.12, 205.13, 205.17, 205.22, 205.24, 201.25, 201.26, 201.27, 201.28, 204.18; 62/534, 79, 4, 89, 477, 480

[56] References Cited

U.S. PATENT DOCUMENTS

| | | | |
|---|---|---|---|
| 3,385,293 | 5/1968 | Phillips | 128/204.16 |
| 3,527,214 | 9/1970 | Rio et al. | 128/204.15 |
| 3,646,934 | 3/1972 | Foster | 128/204.16 |
| 3,650,269 | 3/1972 | Curtis | 128/204.15 |
| 4,080,103 | 3/1978 | Bird | 128/204.16 |
| 4,300,547 | 11/1981 | Pasternack | 128/204.15 |
| 4,314,566 | 2/1982 | Kiwak | 128/204.15 |
| 4,635,629 | 1/1987 | Thorp et al. | 128/204.15 |
| 4,752,310 | 6/1988 | Maier-Laxhuber et al. | 62/66 |

FOREIGN PATENT DOCUMENTS

| | | | |
|---|---|---|---|
| 0148543 | 7/1985 | European Pat. Off. | 128/204.15 |
| 1957176 | 7/1965 | Fed. Rep. of Germany . | |
| 1936651 | 9/1970 | Fed. Rep. of Germany | 128/204.15 |
| 3425419A1 | 1/1986 | Fed. Rep. of Germany . | |

*Primary Examiner*—Edgar S. Burr
*Assistant Examiner*—Kimberly L. Asher
*Attorney, Agent, or Firm*—McGlew and Tuttle

[57] ABSTRACT

The invention pertains to a cooling device for cooling breathing gas in a respiratory protection device with a heat collector exposed to the breathing gas stream. Such a cooling device is to be improved such that it can be prepared for cooling at any desired time prior to putting the respiratory protection device into operation, and that cold storage of a coolant is not required. The improvement is achieved by designing the heat collector as a storage tank for an evaporable liquid, which can be connected to an evacuated adsorbent container such that the liquid will evaporate while absorbing heat of vaporization, and its vapor is adsorbed on an adsorbent contained in the adsorbent container while releasing heat of adsorption and heat of condensation, wherein the adsorbent container is designed as a cooling body that is arranged outside the breathing gas stream and is intended to release the heat into the surroundings.

14 Claims, 2 Drawing Sheets

COOLING DEVICE FOR COOLING BREATHING GAS IN A RESPIRATORY PROTECTION DEVICE

FIELD OF THE INVENTION

The present invention pertains to a cooling device for cooling breathing gas in a respiratory protection device.

BACKGROUND OF THE INVENTION

In respiratory protection devices, especially those with a closed respiration circuit, the temperature of the breathing gas increases to a value that is hard to tolerate for the user of the device when filters with catalytic or adsorptive effect are used. The sensation of comfort of the user of the device is increased by cooling the breathing gas. A cooling device for cooling the breathing gas has become known from German Utility Patent No. DE-U 1,957,176.

In the prior-art cooling device, the heated breathing gas being discharged from the filter with adsorptive effect is passed through a coolant container provided with cooling fins. The breathing gas now releases excess heat onto a coolant contained in the coolant container. The coolant can be replaced as needed in the form of a cartridge.

It is disadvantageous in the prior-art cooling device that the coolant container must always be filled with the coolant immediately before the respiratory protection device is put into operation. The coolant must be stored in the cool state until use, which entails a considerable logistic expense.

SUMMARY AND OBJECTS OF THE INVENTION

It is an object of the present invention to improve a cooling device for cooling breathing gas in a respiratory protection device with a heat collector exposed to the breathing gas stream such that it can be prepared for cooling at any time prior to the of the respiratory protection device being put into operation, and cold storage of a coolant is not necessary.

This task is accomplished by designing the heat collector as a storage tank for an evaporable liquid. This heat collector can be connected to an evacuated adsorbent container such that the liquid will evaporate while taking up heat of vaporization, and its vapor is adsorbed on an adsorbent contained in the adsorbent container while releasing heat of adsorption and heat of condensation, wherein the adsorbent container is designed as a cooling body that is arranged outside the breathing gas stream and is intended to release heat into the surroundings.

Substances with large internal surfaces, e.g., activated carbon, silica gel, and zeolites, are able to adsorb large amounts of gases, e.g., water vapor, nitrogen, oxygen, carbon dioxide, and low-boiling hydrocarbons. The heat of condensation and adsorption thus released lead to an intense increase in the temperature of the adsorbent. A device operating according to this principle for heating or cooling, e.g., foods, has been known from West German Offenlegungsschrift No. DE-OS 34,25,419. A first evacuated container contains a zeolite. This adsorbent container is connected via a valve to a storage tank, in which water and water vapor are in thermodynamic equilibrium. When the valve is opened, the water vapor flows from the storage tank into the adsorbent container, and is adsorbed on the zeolite there while releasing energy. More water will then evaporate in the storage tank, as a result of which the remaining water will be intensely cooled. The water vapor formed is again adsorbed by the zeolite until the zeolite becomes saturated with water. The adsorbed water can again be desorbed from the saturated zeolite by heating the adsorbent container. The water vapor thus formed is then condensed in the storage tank by cooling it, and the valve is closed. The device is thus regenerated for repeated use.

The use of such a device as a cooling device for cooling the breathing gas in a respiratory protection device offers many advantages. Thus, a regenerated cooling device, which is consequently ready to use, can be introduced into a respiratory protection device, and can be put into operation at any time later. As long as the valve is closed, the cooling device remains fully able to cool. Cold storage of coolants is also unnecessary. After use, the cooling device can be regenerated by heating the adsorbent container, for example, by bringing it into contact with an electrical heater or a flame, after which it is completely ready for use. Consequently, no waste is generated during the operation of this cooling device, and it can be repeatedly used without further maintenance.

The use of zeolites as adsorbents and of water as a liquid, is advantageous because a large amount of energy, equaling ca. (around) 110 Wh (Watt-hour) per kg of weight of the device, can be stored as a consequence of the very high adsorption coefficient of zeolites for water. As a result, the cooling device may have a compact and lightweight design, and at equal weight, a longer service life can be achieved than when, e.g., alcohols or liquids are used. Furthermore, such a cooling device can be manufactured at a very low cost, because the substances zeolite and water are inexpensive. In addition, zeolite and water are environmentally highly favorable, because they are nontoxic, and no particular precautionary measures need be taken in connection with their processing.

The valve via which the storage tank can be connected to the adsorbent container may be designed as a hand-operated valve. The user of the device will thus be able to open the valve immediately when putting the respiratory protection device into operation, and thus achieve cooling of the breathing gas from the beginning. However, he can also wait until the breathing gas temperature has reached an uncomfortably high value, and open the valve only thereafter. This leads to prolongation of the service life of the cooling device. The service life can be further prolonged by the user of the device periodically closing the valve when the breathing gas temperature has been reduced to a sufficiently low value.

Forced opening of the valve when putting the respiratory protection device into operation can be mentioned as another variant of the valve opening mechanism. To achieve this, the valve must be mechanically coupled with an element of the respiratory protection device, which element is actuated on start-up. For example, the valve of an oxygen cylinder integrated in the respiratory protection device can be considered in this connection. The advantages of forced opening of the valve are simple design along with high reliability of operation.

The liquid contained in the storage tank must not swash to and fro during the movement of the respiratory protection device, because it could flow into the adsorbent container through the connection line. However, only the vapor of the liquid may enter the adsorbent container, because otherwise no cooling effect would occur in the storage tank. By packing the storage tank of the connection channel between the storage tank and the adsorbent container with an adsorbent material, e.g., a sponge or a nonwoven material, the liquid can be prevented from swashing and running over.

It is a further object of the invention to provide a cooling device for cooling breathing gas in a respiratory protection device which is simple in design, rugged in construction and economical to manufacture.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which a preferred embodiment of the invention is illustrated.

BRIEF DESCRIPTION OF THE DRAWINGS In the drawings.

DETAILED DESCRIPTION OF THE PREFERRED EMBODIMENT

Figure 1:
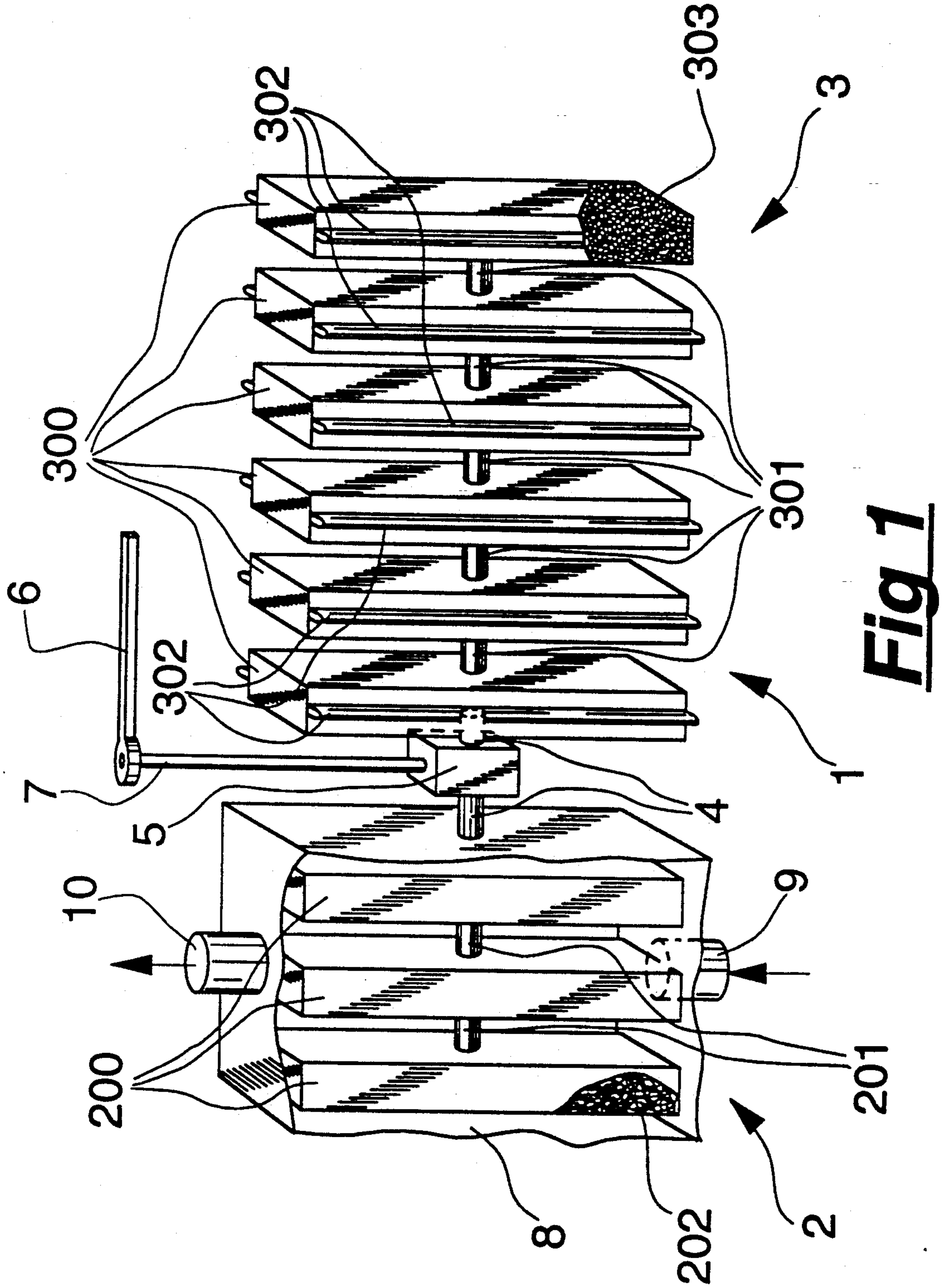
FIG. 1 is a schematic representation of the design of a cooling device according to the invention.

Referring to the drawings in particular, the invention comprises a cooling device 1 shown in FIG. 1 including a storage tank 2, an adsorbent container 3, and a valve 5 arranged in a connection line 4 between said two containers 2, 3.

To enlarge the heat exchange surface, said two containers 2, 3 are subdivided into a plurality of parallelepipedic partial components 200, 300, and these are connected with one another by means of short pipe sections 201, 301. Instead of subdivision into partial components, it would also be possible to provide each container 2, 3 with cooling fins to enlarge the heat exchange surface. The internal spaces of said partial containers 200 are filled with a water-absorbing nonwoven material 202 in order to prevent the water contained in said storage tank 2 from swashing.

Figure 2:
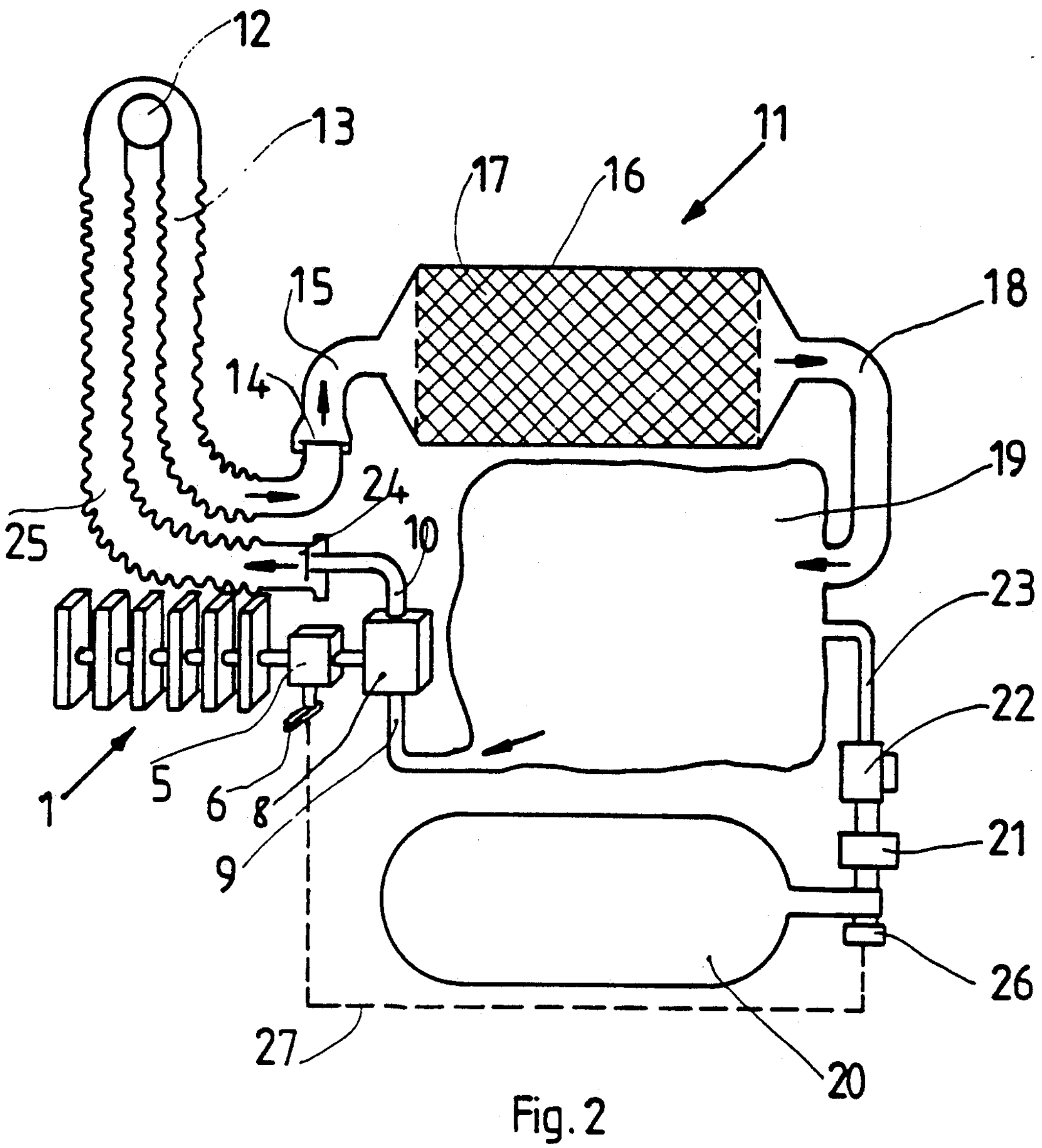
FIG. 2 is a schematic representation showing a respiratory protection device with an integrated cooling device.

Said valve 5 is provided with an operating lever 6, which is connected to the valve via a connecting rod 7. Said storage tank 2 is surrounded by an air guiding box 8, which has an air inlet opening 9 and an air outlet opening 10 for the breathing gas. The air inlet opening is connected to a breathing bag 19, and the air outlet opening is connected to the inspiration tube 25 (FIG. 2).

The function of said cooling device 1 is as follows:

Said storage tank 2 contains water, which is completely adsorbed by a nonwoven material 202, and water vapor, which is in thermodynamic equilibrium with it. Said evacuated adsorbent container 3 contains anhydrous zeolite 303, and said valve 5 is initially closed. Said cooling device 1 is ready to operate in this state and can be stored for any length of time.

When cooling is to be brought about, said valve 5 is opened, and water vapor flows from said storage tank 2 into said adsorbent container 3, and is adsorbed there by the zeolite while heat of condensation and adsorption is released. Due to the reduced pressure in said storage tank 2, water will evaporate, and the temperature of the remaining water, and consequently also of the entire storage tank 2, will decrease because of the heat of vaporization to be used, and the water vapor generated will again be adsorbed by said zeolite 303. This continues until said zeolite 303 becomes saturated with water or the water reserve is consumed. Cooling can also be interrupted by temporarily closing said valve 5.

Since the adsorption capacity of said zeolite 303 decreases with increasing temperature, it is necessary to remove the heat being released during the adsorption. To achieve this, the surface of said adsorbent container 3 is enlarged by subdividing it into a plurality of individual containers 300 and/or providing it with cooling fins 302.

In order to bring the breathing gas to be cooled of a respiratory protection device into contact with said cooled storage tank 2 as effectively as possible, its surface is enlarged, and it is additionally installed in said air guiding box 8. Via said air inlet opening 9, the warm breathing gas enters said air guiding box 8, sweeps said storage tank 2, which is subdivided into a plurality of individual containers 200, and leaves said air guiding box 8 in the cooled state via said air outlet opening 10.

FIG. 2 shows schematically a respiratory protection device 11 with an integrated cooling device 1.

From a connection pipe 12, which is used to connect the device to a breathing mask (not shown), spent breathing gas flows to a regenerating container 16 via an expiration tube 13, an expiration valve 14, and an expiration line 15. This regenerating container contains a carbon dioxide adsorbent 17, which extracts the carbon dioxide from the breathing gas. The breathing gas, which has been freed of the carbon dioxide and heated by the heat of adsorption released, enters a breathing bag 19 via a line 18. The oxygen consumed during respiration is reintroduced into said breathing bag 19 from an oxygen cylinder 20 via a pressure reducer 21 and a metering device 22 through an oxygen line 23. During breathing in, the breathing gas is sent from here to said air inlet opening 9 of said air guiding box 8 of said cooling device 1, the breathing gas flows through said air guiding box 8 while being cooled, and leaves it through said air outlet opening 10. From here, the breathing gas reaches said pipe connection 12 via an inspiration valve 24 and an inspiration tube 25, and furthermore, a breathing mask (not shown).

Figure 3:
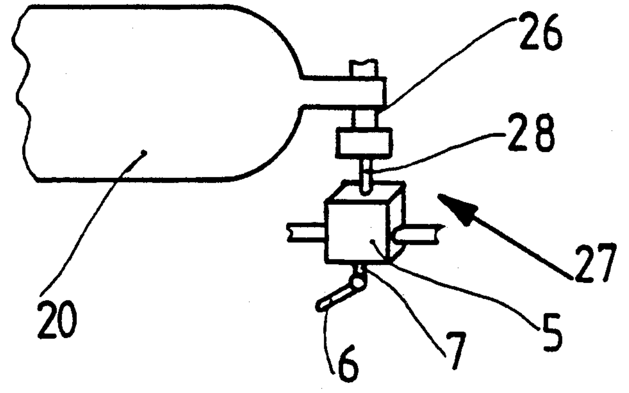
FIG. 3 is a schematic representation showing the coupling of two valves as a detail.

Said valve 5 of said cooling device 1 may be opened by hand via said operating lever 6. As an alternative to this, said valve 5 can also be opened automatically along with the opening of the cylinder valve 26. The mechanical coupling required for this between said two valves 5, 26 is indicated by a broken line. This coupling can also be realized by designing said two valves 5, 26 as a double valve 27, which design is schematically represented in FIG. 3. Said cylinder valve 26 mounted on said oxygen cylinder 20 has an extended shaft 28, which participates in the rotary movement during the opening of said cylinder valve 26 and is connected to said connecting rod 7 of said valve 5, which connecting rod is equiaxial with the shaft 28 and passes through said valve 5. Using said operating lever 6 of said valve 5, said two valves 5, 26 are operated simultaneously in the form of a double valve 27.

The spatial arrangement of said cooling device 1 above the lowest point of said breathing bag 19 has the advantage that water of condensation that may have formed in said cooling device 1 is able to flow into said breathing bag 19 and can be drawn off from there via a bleeding valve (not shown).

While a specific embodiment of the invention has been shown and described in detail to illustrate the application of the principles of the invention, it will be understood that the invention may be embodied otherwise without departing from such principles.

What is claimed is:

1. A cooling device for cooling breathing gas in a respiratory protection device, comprising: an inspiration tube and an expiration tube connected to a user connection pipe; a regenerating container with a carbon dioxide adsorbent connected to said expiration tube, said regenerating container having a gas exit line; an air guiding box connected to said regenerating container gas exit line, and connected to said inspiration tube; a heat collector formed as a storage tank for an evaporable liquid, said storage tank being positioned in said guiding box for heat transfer with breathing gas passing through said guiding box; an evacuated adsorbent container connected to said storage tank, said adsorbent container including an adsorbent for adsorbing vapor evaporated in said storage tank, while absorbing heat of vaporization, said adsorbent container being formed as a cooling body arranged outside of said guiding box for releasing heat of adsorption and heat of condensation to a region surrounding said cooling body.

2. A cooling device according to claim 1, wherein said adsorbent is a zeolite and said liquid is water.

3. A cooling device according to claim 2, wherein said storage tank and said adsorbent container are connected via a valve that can be operated by hand.

4. A cooling device according to claim 1, further comprising a valve connected between said storage tank and said adsorbent container for selectively providing communication between said storage tank and said adsorbent container.

5. A cooling device according to claim 1, further comprising a valve connecting said storage tank and said adsorbent container, said valve including means for automatically providing communication between said storage tank and said adsorbent container when connected to an element to be operated when said respiratory protective device is put into operation.

6. A cooling device according to claim 5, wherein said valve is provided combined with a cylindrical valve of a gas cylinder, said gas cylinder being integrated to form a double valve for opening communication between said adsorbent container and said storage tank jointly with opening of said gas cylinder.

7. A cooling device according to claim 1, further comprising an adsorbent material disposed in said storage tank for completely adsorbing said liquid and releasing said vapor of said liquid.

8. A cooling device according to claim 1, wherein said storage tank and said adsorbent container are provided with fins to provide an enlarged heat exchange surface.

9. A cooling device according to claim 1, wherein said storage tank and said adsorbent container are subdivided into a plurality of individual subcontainers which are connected to one another by tubes.

10. A cooling device for cooling breathing gas in a respiratory protective device, comprising:

an inspiration tube and an expiration tube connected to a user connection pipe;

a regenerating container with a carbon dioxide adsorbent connected to said expiration tube, said regenerating container having a gas exit line;

an air guiding box connected to said regenerating container gas exit line, and connected to said inspiration tube;

a breathing bag connected between said regenerator and said guiding box;

an oxygen container connected to said breathing bag for supplying oxygen to said breathing bag;

a heat collector including a plurality of storage tanks joined by a common conduit, each of said storage tanks containing adsorbent material and liquid completely adsorbed by said adsorbent material, each of said storage tanks being disposed in said guiding box;

an evacuated adsorbent structure including a plurality of adsorbent containers connected to each other via said common conduit and connected to said storage tanks via said common conduit, said adsorbent containers including an adsorbent for adsorbing the vapor evaporated in said storage tank, while absorbing heat of vaporization, said adsorbent containers being formed as a cooling body arranged outside of said guiding box for releasing heat of adsorption and heat of condensation to a region surrounding said cooling body; and control means connected to said common conduit for blocking communication between said adsorbent containers and said storage tanks.

11. A cooling device according to claim 10, wherein said adsorbent in said adsorbent containers is a zeolite and said liquid is water.

12. A cooling device according to claim 10, wherein said control means is a valve connected in said common conduit between said storage tank and said adsorbent container for selectively providing communication between said storage tank and said adsorbent container.

13. A cooling device according to claim 12, wherein said valve is provided combined with a cylinder valve of a gas cylinder of said oxygen container to form a double valve for opening communication between said adsorbent containers and said storage tank jointly with opening of said oxygen container.

14. A cooling device according to claim 10, wherein each of said storage tanks and each of said adsorbent containers include fins providing an enlarged heat transfer surface.

* * * * *